(12) United States Patent
Jaskolski et al.

(10) Patent No.: US 9,868,887 B1
(45) Date of Patent: Jan. 16, 2018

(54) GRIP ENHANCING COMPOSITION

(71) Applicants: Kimberly D. Jaskolski, Irwin, PA (US); Dena Ann Woodworth, Los Angeles, CA (US)

(72) Inventors: Kimberly D. Jaskolski, Irwin, PA (US); Dena Ann Woodworth, Los Angeles, CA (US)

( * ) Notice: Subject to any disclaimer, the term of this patent is extended or adjusted under 35 U.S.C. 154(b) by 0 days.

(21) Appl. No.: 15/729,154

(22) Filed: Oct. 10, 2017

Related U.S. Application Data

(63) Continuation-in-part of application No. 14/543,852, filed on Nov. 17, 2014, now Pat. No. 9,782,887.

(51) Int. Cl.
*A61K 8/00* (2006.01)
*C09K 3/14* (2006.01)
*C08L 1/28* (2006.01)
*C08L 93/04* (2006.01)

(52) U.S. Cl.
CPC .............. *C09K 3/149* (2013.01); *C08L 1/284* (2013.01); *C08L 93/04* (2013.01)

(58) Field of Classification Search
CPC ........ A61K 9/1161; A61K 8/585; A61K 8/73; A61K 8/91; A61K 36/81; A61K 31/475; A61K 31/685; A61Q 1/14; A61Q 5/00; A61Q 5/12; A61Q 11/02; A61Q 19/007; A61Q 19/5002; A61Q 5/02; A61Q 5/10
See application file for complete search history.

(56) References Cited

U.S. PATENT DOCUMENTS 6,183,766 B1 * 2/2001 Sine ..................... A61K 8/0208
424/401

* cited by examiner

*Primary Examiner* — Nannette Holloman
(74) *Attorney, Agent, or Firm* — Gary P. Topolosky

(57) ABSTRACT

A composition/formula for enhancing the grip of certain athletes and professionals to hold or otherwise "stick" onto an object like a piece of sports equipment, a tool handle or an exercise mat. The composition consists of: a magnesium carbonate base to which are added a natural gum rosin, isopropyl alcohol, hydroxyl ethyl cellulose (a plant-based thickener) and a carrier oil, preferably jojoba oil. A limited amount of candelilla wax may be blended therewith.

20 Claims, 2 Drawing Sheets

GRIP ENHANCING COMPOSITION

CROSS-REFERENCE TO RELATED APPLICATION

This application is a continuation-in-part of U.S. patent application Ser. No. 14/543,852, filed on Nov. 17, 2014, the disclosure of which is fully incorporated by reference herein.

FIELD OF THE INVENTION

The present invention relates to a composition for enhancing an individual's ability to grasp, adhere or otherwise "stick" to an object, especially a sports object. More particularly, this invention relates to a magnesium carbonate-based formula to which other components are purposefully (and, in some instances, optionally) added with the end result being applied to one's hands (or feet) and/or directly to the sports object itself, such as the handle to a golf club or racket (tennis, racquetball, etc.) for better gripping. Additionally, this paste-like composition may be applied to certain tools (like a hammer) for firmer gripping.

BACKGROUND OF THE INVENTION

The ability to grasp an object is important when using sports equipment and/or when working with certain hand tools. Securely grasping equipment/tools so that they do not slip helps ensure proper use. Specifically, the ability to firmly grip a club, bat or racket handle enables its use to compete more confidently and often more successfully.

Also, the ability to grasp a hand tool ensures that the task for which it is being used is properly, more efficiently performed, such as hammering a nail straight into a piece of wood. In addition, the ability to securely grip/hold sports equipment or tools helps prevent injuries that might otherwise occur if/when the equipment or tool slips out of one's hand(s).

The composition causes static friction which aids in keeping the body from sliding, slipping and/or otherwise moving unintentionally. It also suppresses sweat where applied thus further aiding in sports performance.

This composition does not wear off with sweat nor by wiping one's hands and feet with a cloth. It is preferably removed using a surfactant and water. In addition, this composition does not leave residue when thoroughly dried. It will, however, give its users the ability to focus on the primary foundations their sport. It is known to use gloves or surface treatments like chalk, resins or adhesives to help securely grasp sports equipment or tools. However, gloves, chalk, resins and adhesives suffer from several drawbacks. Gloves can impede rather than aid in one's ability to securely grasp an object, however. Sometimes, the very thickness of the glove itself interferes with its wearer's ability to feel and thus control the object being held. Chalk, and certain known resins/adhesives, like pine tar, can be messy to apply and stain tools, equipment and clothing. Accordingly, there exists a need for a substance which can be quickly, easily and neatly applied to tools and equipment and which will improve one's ability to grasp or otherwise stick to objects. It is a primary object of this invention to meet that need and provide such a compound/substance.

Certain granular-based compositions are known to prevent persons from falling while walking on slippery surfaces, and in some manufacturing processes. Examples of such compositions include: Lund U.S. Pat. No. 4,528,231 for a slip and wear resistant flooring and composition and method for producing the same. That composition includes coarse metallic particles applied to a sub-floor for preventing individuals from slipping thereon.

Hunt U.S. Pat. No. 5,395,673 discloses a non-slip composition and method of application to a ground surface where lighting conditions are poor. That composition includes an aluminum oxide aggregate for preventing slippage and a phosphorescent pigment to illuminate the ground surface.

Kincaid U.S. Pat. No. 5,451,446 discloses a thermosetting binder for an abrasive article, said binder including a cured epoxy to bond abrasive grades together and form a shaped mass. Alternatively, that epoxy holds and supports abrasive grains onto a sheet.

Feronato U.S. Pat. No. 5,654,078 discloses an abrasive member for dry-grinding and polishing. That member includes metal deposits in which abrasive particles have been imbedded.

Still other known compositions include the moisture-absorbing composition and related method of Sereboff U.S. Pat. No. 5,565,023. That composition combines a majority of magnesium or calcium carbonate with sawdust particles.

A sports-specific grip enhancer was the subject of Maynard PCT Application No. WO 99/43492. It taught a granular mix of aluminum oxide, silicon carbide, silica and sand for applying to golf club handles and the like.

In West PCT Application No. WO 00/78889, a medically-specific gripping condition is addressed using a composition/formula that combines water with one or more listed starches.

Finally, there is the antiperspirant/gripping composition of Plunk PCT Application No. WO 06/63114. It entailed mixing aluminum chlorohydroxide and aluminum hydroxyl chloride dihydrate in water or another specially formulated base.

Most of the foregoing compositions are directed towards anti-slip or manufacturing processes. None specifically address helping improve a person's ability to securely grasp an object especially a sports-related item surrounding materials and the wearer's clothes. It is an object of this invention to provide such a composition/formula.

SUMMARY OF THE INVENTION

One embodiment of this invention, to be made and sold as Liquid Friction™, is ideally suited for helping an individual to improve on his/her sport by reducing the chance of slippage thereon and any corresponding injuries resulting therefrom. This first preferred composition stops its wearer/user from overly sweating from his/her palms and feet. When the wearer/user towels off (mid-routine), this product is known to reconstitute itself. And by helping exercisers more firmly adhere to their respective exercise areas.

Main elements of this composition/formula include a magnesium carbonate base to which are added: a natural gum rosin, isopropyl alcohol, hydroxyl ethyl cellulose (a plant-based thickener) and a carrier oil (for consistency). Optionally, a slight amount of candelilla wax may be blended in before the entirety is mixed together and allowed to set.

BRIEF DESCRIPTION OF THE DRAWINGS

A more complete understanding of the present invention may be obtained from a consideration of the following description made in conjunction with the accompanying drawing in which.

DESCRIPTION OF PREFERRED EMBODIMENTS

With respect to the main, preferred embodiment of composition/formula according to this invention, there is provided a base component made from magnesium carbonate. One version of the same is made and sold by Mammut as Liquid Climbing Chalk. Alternate versions from other commercial manufacturers include Liquid Grip and Tite Grip.

For one representative sample size of this composition, weighing about 1 to 2 oz., it is preferred to keep main ingredient, $MgCO_3$ powder levels between about 0.125 to 1.75 oz, and more preferably about 0.5 oz. To that primary component, there is first added a compatible natural gum rosin. Preferred amounts of that component range from 0.45 to 1.95 oz., with a more preferred level between about 1 and 1.35 oz. One representative version of such rosins is made and sold under the name Liquid Grip. An alternate version is made and sold as Muellers Magic Grip.

Compositionally, the third main ingredient to be added to the foregoing blend of $MgCO_3$ and Rosin is isopropyl alcohol. For the aforementioned, representative sample size, it may be added to between about 30-95 ml per "batch", with a more preferred level being about 60 ml.

Next, there is added hydroxyl ethyl cellulose or "HEC" in relative quantities of about 0.25 to 0.75 tsp, more preferably about 0.5 tablespoon per batch.

To the foregoing "soup", it is preferred to add a customizable blend of a carrier oil for fragrance and consistency: about ¼-1 teaspoon carrier oil such as avocado oil, sunflower seed oil, grape seed oil, jojoba oil, olive oil and sweet almond oil. Most preferably, it is jojoba oil. But this composition contains no essential oils.

On an optional basis, it has been determined that slight quantities of candelilla wax, around ½ tsp per batch, make the aforementioned composition more suitable for water uses/activities, including: SUP, surfing, white water rafting, etc.

EXAMPLE

In the particular manufacture of one representative batch sampling, sized about 1 oz. total, the following process steps are taken.

The magnesium and rosin are combined then the alcohol gradually mixed therein for about 1 min. HEC is added and mixed for another minute. The carrier oil and other components are added, mixed and the entirety allowed to set for several minutes before packaging.

To a lesser degree, it may be possible (though not preferred) to administer some amount of the composition to certain areas (i.e., where the yogi's hands and feet "start" for exercising) of the sport. For future applications (and sponsorship tie-ins), mats/pads may be pre-printed with regions/rectangles onto which gripping compounds like the present invention may be repeatedly applied. As the component combination above will not permanently stain such mats (or the exerciser's apparel), it is understood that such mats/pads may be made from various cushioned materials, including those custom covered with leather, vinyl, rubber, plastic, or other known alternatives.

Figure 1:
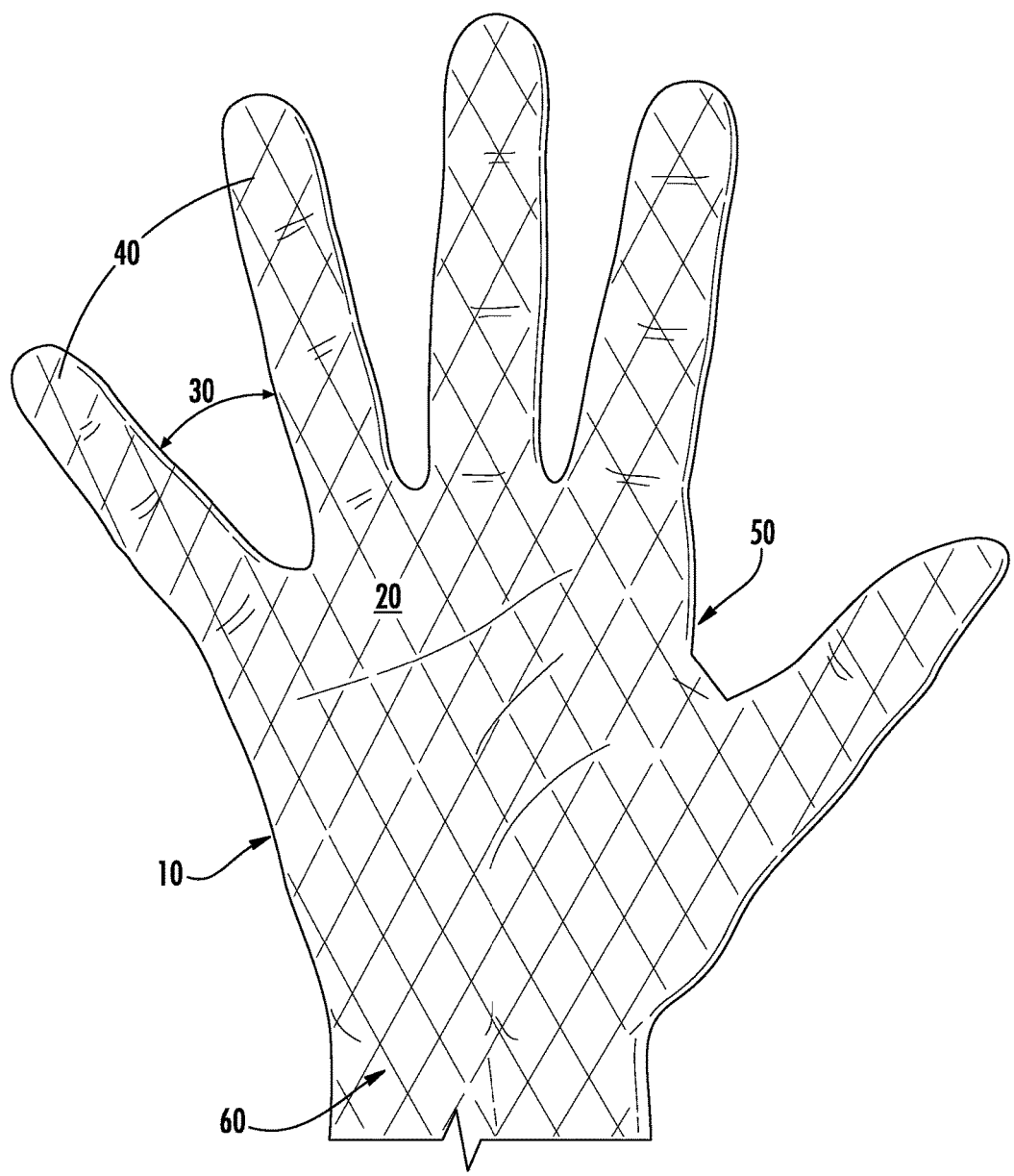
FIG. 1 is a front schematic view of the palm or inside to a human hand showing where this gripping composition should be rubbed on prior to the start of a yoga exercise routine.

When the foregoing composition is applied to a user's hands/palms and feet (in place of or in addition to a pre-applied pad working zone), one representative area for hand/palm application is illustrated in accompanying FIG. 1. Particularly therein, the user's bare hand 10 is shown with the composition 20 applied liberally about the fingers 30, fingertips 40 and palm 50 all the way down to his/her wrist 60. Note how the inside fingers and palms are covered down to the wrists. In practice, the application of composition, as shown, starts by applying a small dab (amount) onto one of the hands. Then both palms are rubbed together for coating the entire inner hand surface. It is advised that application be done (performed) quickly, especially to the fingers, fingertips, palm pads and other main pressure points. The same rules should be followed for compositional applications to the bottoms of one's feet.

Though shown for topical hand/feet applications, it is understood that this same composition/formula has other sports-related end uses. A typical golf club or handball/squash/tennis racket handle is most evident. Still other sporting equipment candidates include but are not limited to: baseball bats, hockey sticks, fishing rods and weight lifting bars. Though not equipment specific, but rather end user-related, it is anticipated that hand and foot alternative applications might further include professional and/or recreational wall climbers, kick boxers and other martial artists. In addition, there are benefits when used by gymnasts, professional card dealers and bankers (currency handlers). It may also help gripping when used by those wearing rubber gloves for certain handlers and/or medical personnel.

Figure 2:
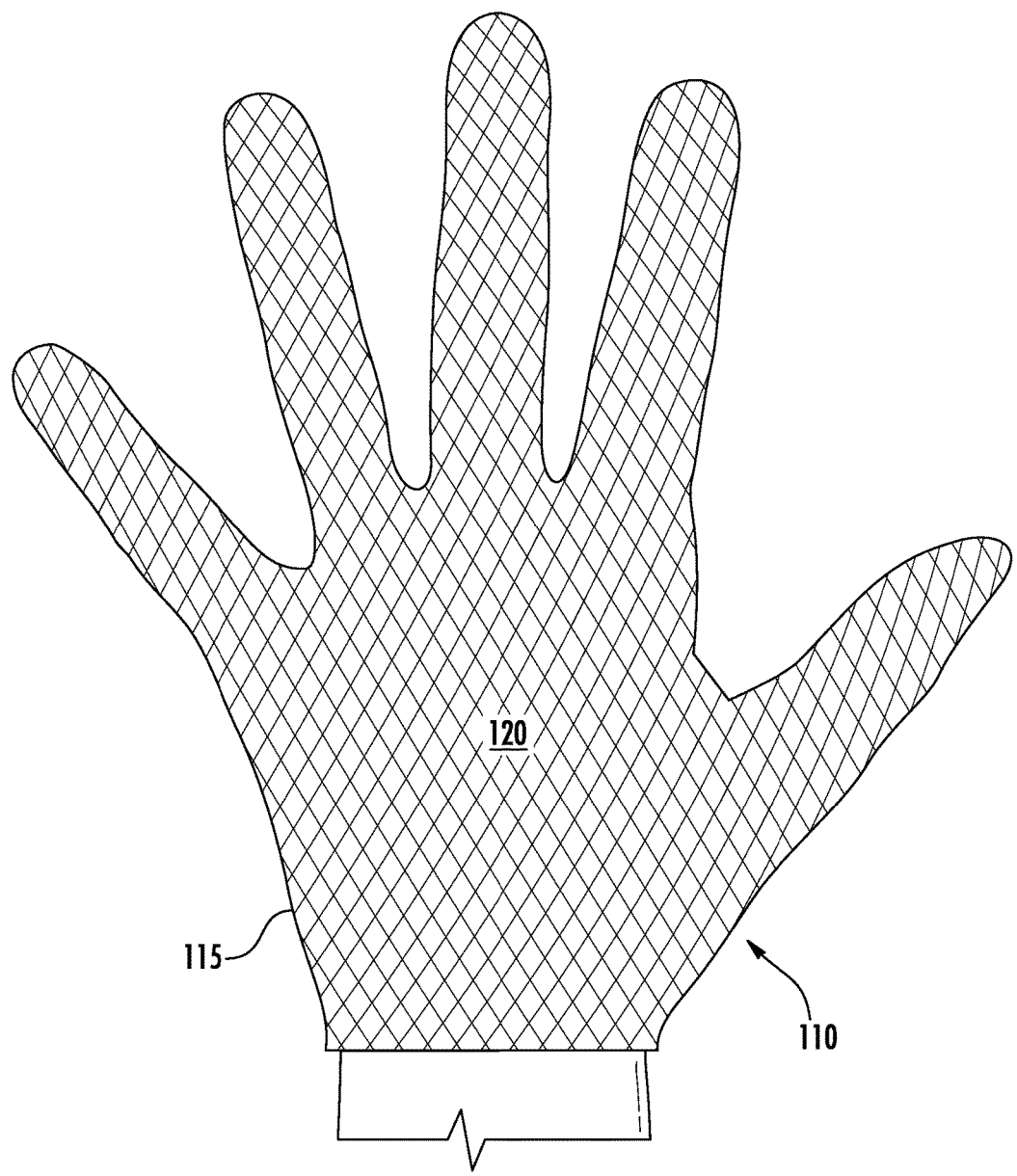
FIG. 2 is a front schematic view of a gloved human hand showing where this gripping composition should be rubbed on prior to the start of an athletic activity and/or gripping of athletic equipment.

FIG. 2 shows a similar application to that of FIG. 1 except that in this second instance, the user's hand 110 is covered by a glove 115 onto which composition 120 is applied and the user's gloved hands rubbed together. It may also help gripping when used by those wearing rubber gloves for certain dental handlers, caregivers, surgeons and/or other medical personnel.

It is also understood that this same composition/formula may have other non-sports applications such as for those handling working tools on a regular basis . . . professional carpenters (for hammers), certain mechanics (wrenches and drills), electricians (pliers) and/or painters (brushes and/or rollers). For that matter, it is possible to make and sell compositional variations (that are non-allergenic) for medical and/or dental instruments.

Needless to say, the same composition that works directly on one's hands can be applied to certain surface areas of a glove fitted over that same hand. To that extent, and to the point where playing rules allow, it is understood/expected that this same composition can be applied over the gloves of football players to more securely grasp a football, or soccer goalies to more securely grasp a soccer ball.

IN the appended claims, one preferred composition is disclosed in component ratios for a 2 ounce portion "serving" size. It is to be understood, however, that still other sizes and component ratios should be readily calculated from the 2 oz. example. For instance, packaging may enable individual tubes of compositions ranging from 0.5 oz. each, to 1 oz. sizes, or in an economy setting, for use in yoga studios and/or outdoor playing fields/courts, sizes of about 5 oz. each, up to about 10, 15 or 20 oz. bottles.

Numerous modifications to and alternative embodiments of the present invention will be apparent to those skilled in the art in view of the foregoing description. Accordingly, this description is to be construed as illustrative only and is for the purpose of teaching those skilled in the art the best mode of carrying out the invention. Details of the structure may be varied substantially without departing from the spirit of the invention and the exclusive use of all modifications that come within the scope of the appended claims is reserved.

What is claimed is:

1. A composition for enhancing an individual's grip onto a surface or a hand-held object, a 2 ounce portion size of said composition comprising:
   a base of between about 0.5 and 1.25 oz. of magnesium carbonate;
   a natural gum rosin;
   isopropyl alcohol;
   hydroxyl ethyl cellulose; and
   one or more carrier oils.

2. The composition of claim 1 wherein the carrier oil is selected from the group consisting of: an avocado oil, a grape seed oil, a sweet almond oil, a sunflower seed oil, a jojoba oil and an argon oil.

3. The composition of claim 2 wherein the carrier oil is jojoba oil.

4. The composition of claim 1, which further contains a candelilla wax.

5. The composition of claim 1 wherein said hand-held object is apiece of sports equipment.

6. The composition of claim 5 wherein said piece of sports equipment is selected from the group consisting of a golf club, a racket, a ball bat, a fishing rod and a hockey stick.

7. The composition of claim 1 wherein said hand-held object is a working tool selected from the group consisting of a hammer, a wrench, a paint brush and a paint roller.

8. The composition of claim 1, which is free of any essential oils.

9. A composition for applying to an individual's hands for enhancing the individual's grip to a yoga mat or a piece of sports equipment, a 2 oz. portion size of said composition comprising:
   between about 0.125 and 1.25 oz. of magnesium carbonate powder;
   between about 0.75 to 1.85 oz. natural gum rosin;
   between about 30-75 ml of isopropyl alcohol;
   hydroxyl ethyl cellulose; and
   one or more carrier oils selected from the group consisting of: an avocado oil, a grape seed oil, a sweet almond oil, a sunflower seed oil, a jojoba oil and an argon oil.

10. The composition of claim 9, which contains about 0.5 oz. magnesium carbonate.

11. The composition of claim 9, which contains about 30 to 75 ml of isopropyl alcohol.

12. The composition of claim 11, which contains about 55 ml of isopropyl alcohol.

13. The composition of claim 9, which contains about 0.25 to 0.75 tablespoon of HEC (hydroxyl ethyl cellulose).

14. The composition of claim 13, which contains about 0.5 tablespoon of HEC (hydroxyl ethyl cellulose).

15. The composition of claim 9 wherein the carrier oil is jojoba oil.

16. The composition of claim 9, which further contains a candelilla wax.

17. A method for enhancing an individual's grip to a piece of sporting equipment, said method comprising:
   (a) providing a composition, a 2 oz. portion size of which would contain: between about 0.125 and 1.25 oz. of magnesium carbonate powder, between about 0.75 to 1.85 oz. natural gum rosin, between about 30-75 ml of isopropyl alcohol, hydroxyl ethyl cellulose, and one or more carrier oils selected from the group consisting of: an avocado oil, a grape seed oil, a sweet almond oil, a sunflower seed oil, a jojoba oil and an argon oil; and
   (b) applying the composition to a surface that will contact with the piece of sporting equipment.

18. The method of claim 17 wherein step (b) includes applying the composition directly to the individual's hands and fingers.

19. The method of claim 17 wherein step (b) includes applying the composition onto a pair of gloves worn by the individual.

20. The method of claim 17 wherein the carrier oil in the composition is jojoba oil.

\* \* \* \* \*